US012618759B2

(12) United States Patent
Li et al.

(10) Patent No.: US 12,618,759 B2
(45) Date of Patent: May 5, 2026

(54) HIGH-PRESSURE LIQUID DELIVERY SYSTEM UNDER HIGH CENTRIFUGAL ACCELERATION CONDITION ON ARM-CENTRIFUGE

(71) Applicant: ZHEJIANG UNIVERSITY, Hangzhou (CN)

(72) Inventors: Jinlong Li, Hangzhou (CN); Daosheng Ling, Hangzhou (CN); Jianjing Zheng, Hangzhou (CN); Yubing Wang, Hangzhou (CN); Yu Zhao, Hangzhou (CN); Chuang Zhao, Hangzhou (CN); Lujun Wang, Hangzhou (CN); Jian Wang, Hangzhou (CN); Zizhuang Yan, Hangzhou (CN); Bingjing Qiu, Hangzhou (CN); Yunmin Chen, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 308 days.

(21) Appl. No.: 18/430,659

(22) Filed: Feb. 2, 2024

(65) Prior Publication Data

US 2024/0167925 A1     May 23, 2024

Related U.S. Application Data

(63) Continuation of application No. PCT/CN2022/073802, filed on Jan. 25, 2022.

(51) Int. Cl.
G01N 33/24 (2006.01)
G01N 3/08 (2006.01)

(52) U.S. Cl.
CPC .............. G01N 3/08 (2013.01); G01N 33/24 (2013.01); G01N 2203/0037 (2013.01)

(58) Field of Classification Search
CPC ........................................................ G01N 3/08
(Continued)

(56) References Cited

U.S. PATENT DOCUMENTS

2008/0271786 A1     11/2008   Howell

FOREIGN PATENT DOCUMENTS

CN            1916476 A      2/2007
CN         101601875 A     12/2009
(Continued)

OTHER PUBLICATIONS

Chen et al. Machine translation of CN 205714764 U. Published Nov. 2016. Accessed Jan. 2026. (Year: 2016).*
(Continued)

*Primary Examiner* — Walter L Lindsay, Jr.
*Assistant Examiner* — Philip T Fadul
(74) *Attorney, Agent, or Firm* — Wiersch Law Group

(57)     ABSTRACT

A high-pressure liquid delivery system under a high centrifugal acceleration condition on an arm-centrifuge, comprising a centrifuge main engine, a ground liquid source, a ground delivery conduit, a centrifuge bottom rotary joint, a centrifuge rotary arm delivery conduit, a rotary arm-basket pin roll, a basket rotary joint, a basket delivery conduit and a basket conduit outlet. According to the present disclosure, the basket rotary joint is introduced to adapt to the change of the basket-rotary arm angle before and after the arm-type basket centrifuge works, so that the demand for water, electricity, oil and gas transportation of the centrifuge is met. Therefore, the design for the conduit of the centrifuge-basket part is solidified, and compared with the traditional solution that a high-pressure hose is connected to the basket, the centrifugal acceleration load of the load can be increased to more than 500 g.

4 Claims, 2 Drawing Sheets

(58) Field of Classification Search
USPC .......................................................... 73/784
See application file for complete search history.

(56)                    References Cited

FOREIGN PATENT DOCUMENTS

| CN | 102421520 | A |   | 4/2012 |
| CN | 103234733 | A |   | 8/2013 |
| CN | 103267193 | A |   | 8/2013 |
| CN | 103836195 | A |   | 6/2014 |
| CN | 104105915 | A |   | 10/2014 |
| CN | 105021795 | A |   | 11/2015 |
| CN | 205714764 | U | * | 11/2016 |
| CN | 106838513 | A |   | 6/2017 |
| CN | 108561655 | A |   | 9/2018 |
| CN | 109092573 | A |   | 12/2018 |
| CN | 109225681 | A |   | 1/2019 |
| CN | 109682688 | A |   | 4/2019 |
| CN | 110192059 | A |   | 8/2019 |

| CN | 110302906 | A |   | 10/2019 |   |
| CN | 111207998 | A | * | 5/2020 | ............. G01N 3/02 |
| CN | 213018267 | U |   | 4/2021 |   |
| CN | 113309917 | A |   | 8/2021 |   |
| CN | 215060330 | U |   | 12/2021 |   |
| JP | 2005021849 | A |   | 1/2005 |   |
| SK | 157592 | A3 |   | 6/1995 |   |

OTHER PUBLICATIONS

Ran et al. Machine translation of CN 111207998 A. Published May 2020. Accessed Jan. 2026. (Year: 2020).*
International Search Report (PCT/CN2022/073802); Date of Mailing: Jun. 22, 2022.
First Office Action(CN202210088905.3); Date of Mailing: Sep. 23, 2022.
Notice Of Allowance(CN202210088905.3); Date of Mailing: Apr. 23, 2023.

* cited by examiner

HIGH-PRESSURE LIQUID DELIVERY SYSTEM UNDER HIGH CENTRIFUGAL ACCELERATION CONDITION ON ARM-CENTRIFUGE

CROSS-REFERENCE TO RELATED APPLICATIONS

The present application is a continuation of International Application No. PCT/CN2022/073802, filed on Jan. 25, 2022, the content of which is incorporated herein by reference in its entirety.

TECHNICAL FIELD

The present disclosure belongs to the field of geotechnical engineering model tests, and in particular relates to a high-pressure liquid delivery system under a high centrifugal acceleration condition on an arm-centrifuge.

BACKGROUND

An arm geotechnical centrifuge is a kind of test equipment used for physical simulation test of geotechnical engineering. The arm geotechnical centrifuge simulates self-weight stress via a centrifugal acceleration generated by high-speed rotation, so that a stress field in the scale model of rock and soil carried in a basket is similar to a large-scale prototype on site. Therefore, the arm geotechnical centrifuge can simulate the stress, deformation and damage of the prototype rock and soil structure, so as to verify the design solution, study the material parameters, verify the mathematical model and numerical analysis results, and explore new physical phenomena of geotechnical engineering. The arm geotechnical centrifuge has been widely used in the field of geotechnical engineering. At present, the related experiments involved include piping, dam-break experiment, offshore structure stability experiment, slope instability experiment, deformation and failure of underground cavern and the like.

In the experiments involving water such as dam break and piping, it is necessary for the centrifuge to provide water supply to the geotechnical model in the basket. Moreover, as the increase of the depth of the studied rock and soil, in addition to the self-weight stress, it is necessary to apply multi-channel pressures such as axial pressure and confining pressure to the studied rock and soil model through multi-channel hydraulic pressure to simulate the stress state of prototype thereof, and put forward the demand for multi-channel oil supply in the centrifuge basket.

The structure of the arm-centrifuge is two baskets hung at the two ends of the horizontal rotating arm perpendicular to the ground. The baskets are perpendicular to the ground/rotary arm before rotary to facilitate loading large-scale experimental devices. However, the baskets are gradually parallel to the ground/rotary arm with the increase of centrifugal acceleration, and the change of the angle brings certain difficulties to the water supply and oil supply in the baskets. In the traditional practice, the water supply and oil supply conduit of the centrifuge is provided with a rigid joint at the end of the rotary arm of the centrifuge connected to a flexible steel wire hose transporting water and oil into the baskets and using the flexibility of the steel wire hose to adapt to the angle difference of the baskets in two states. This hose is referred to "a basket transport hose". It is difficult to properly reinforce the hose due to the position will change before and during the experiment, and the centrifugal acceleration of the whole hose depends almost entirely on the joint with the rotary arm. However, the existing high-pressure tubing and the matching joint are generally designed for internal pressure resistance, and there is no index and ability of tensile strength. On the centrifuge with a large capacity and a high centrifugal acceleration, the safety of the basket delivery hose and the joint cannot be guaranteed. As the improvement of the capacity of experimental device and the increase of centrifugal acceleration, there is a risk of sealing failure or even fracture due to the basket delivery hose and the joint cannot bear the ultra-high centrifugal load eventually.

For example, on the proposed national major scientific and technological infrastructure "Super Gravity Centrifugal Simulation and Experiment Device", the proposed model machine is configured with a maximum centrifugal acceleration of 300 times of the earth's gravity, an effective rotation radius of 6.4 m, a suspended section length of 2.8 m for the basket delivery hose, and a calculated stress of about 370 kg for a 13 mm inner diameter hose under a normal load. The configuration exceeds the design capacity requirements of the high-pressure hose, so it is urgent to propose a new centrifuge high-pressure liquid delivery solution.

SUMMARY

The present disclosure aims to provide a high-pressure liquid delivery system under a high centrifugal acceleration condition on an arm-centrifuge in view of the shortcomings of the prior art.

The object of the present disclosure is realized through the following technical solution: a high-pressure liquid delivery system under a high centrifugal acceleration condition on an arm-centrifuge includes a centrifuge main engine, a ground liquid source, a ground delivery conduit, a centrifuge bottom rotary joint, a centrifuge rotary arm delivery conduit, a rotary arm-basket pin roll, a basket rotary joint, a basket delivery conduit and a basket conduit outlet.

The centrifuge bottom rotary joint is fixed at the bottom of the centrifuge main engine, and a stator end of the centrifuge bottom rotary joint is connected with the ground liquid source by the ground delivery conduit, so that the centrifuge remains motionless during rotation; a rotor end of the centrifuge bottom rotary joint is connected with one end of the centrifuge rotary arm delivery conduit and rotates with the rotation of the centrifuge during the rotation of the centrifuge; the other end of the centrifuge rotary arm delivery conduit is connected with the basket rotary joint.

The basket rotary joint consists of a stator, a stator input interface, a rotor and a rotor output interface; a plurality of arc-shaped launders are engraved on the surface of the rotor; the bottom of each arc-shaped launder is communicated with the rotor output interface; the stator is sleeved outside the rotor; the stator is provided with the stator input interface in an opening at a position corresponding to each arc-shaped launder on the rotor.

The stator of the basket rotary joint is fixedly connected to the rotary arm-basket pin roll, and the stator remains motionless during the rotation of the basket; the stator input interface is connected with the centrifuge rotary arm delivery conduit.

The basket delivery conduit is fixed on the basket, and an interface thereof in the basket is the basket conduit outlet; the basket delivery conduit is rigidly connected with the rotor output interface of the basket rotary joint; and the basket delivery conduit drives the rotor of the basket rotary joint to rotate together during the rotation of the basket, and the stator input interface is always communicated with the arc-shaped launder on the corresponding rotor during the rotation of the rotor relative to the stator, thereby communicating with the rotor output interface.

Further, the ground liquid source includes a hydraulic oil source and a water source.

Further, the ground delivery conduit is connected with the stator end of the centrifuge bottom rotary joint through a sealing threaded port.

Further, a radian of the arc-shaped launder is θ, three arc-shaped launders are uniformly arranged on one circumference of the rotor; taking the three arc-shaped launders as a group, axial annular sealing components are arranged between groups of launders; rounded rectangular sealing components are arranged around the three launders of each group.

Further, the radian θ of the arc-shaped launder satisfies:

$$90° + \frac{360° d}{\pi D} < \theta < 120° - \frac{360° f}{\pi D}$$

where d is the inner diameter of the stator input interface, D is the outer diameter of the rotor, and f is a circumferential safety sealing distance between the launders.

Further, the stator and the rotor are fitted by a ball bearing to rotate relatively by 90 degrees.

The present disclosure has the following advantages and positive effects:

1) A rotary joint is adopted in the liquid delivery conduit in the present disclosure to adapt to the angle change of the basket-rotary arm before and after the arm-type basket centrifuge works, so as to meet the requirements of water, electricity, oil and gas transportation of the centrifuge.

2) Compared with the traditional solution, all airborne devices need to be connected with the end of the rotary arm with long-distance hoses and need additional reinforcement. The conduits in the rotary arm-rotary joint and rotary joint-basket can be made of rigid pipes, and the layout and reinforcement are both solidified. Compared with the traditional solution of connecting high-pressure hoses to the basket, the centrifugal load of the load can be increased to more than 500 g.

3) Since the proposed rotary joint of the basket needs to be fixed at the pin roll of the basket in a cantilever-like manner, the centrifugal acceleration at this position is large, and the traditional rotary joint is too heavy and bulky to be reinforced, and it encroaches on the space in the basket that could have been used for experiments. Therefore, a new rotary joint is designed for the condition that the centrifuge basket rotates only 90 degrees relative to the rotary arm. The annular groove is changed into an arc-shaped groove, and one ring is expanded into three rings. The volume and weight of the rotary joint are reduced by about ⅓, which greatly increases the feasibility of the rotary joint at the pin roll of the centrifuge and the number of accessible pipes.

1 Centrifuge main engine, 2 Ground liquid source, 3 Ground delivery conduit, 4 Centrifuge bottom rotary joint, 5 Centrifuge rotary arm delivery conduit, 6 Rotary arm-basket pin roll, 7 Basket rotary joint, 7-1 Stator, 7-2 Stator input interface, 7-3 Rotor, 7-4 Arc-shaped launder, 7-5 Circumferential sealing component, 7-6 Rotor output interface, 7-7 Annular seal assembly, 7-8 Bearing, 8 Basket delivery conduit, 9 Basket conduit outlet.

DESCRIPTION OF EMBODIMENTS

The specific embodiment of that present disclosure will be further described in detail with reference to the accompanying drawing.

Figure 1:
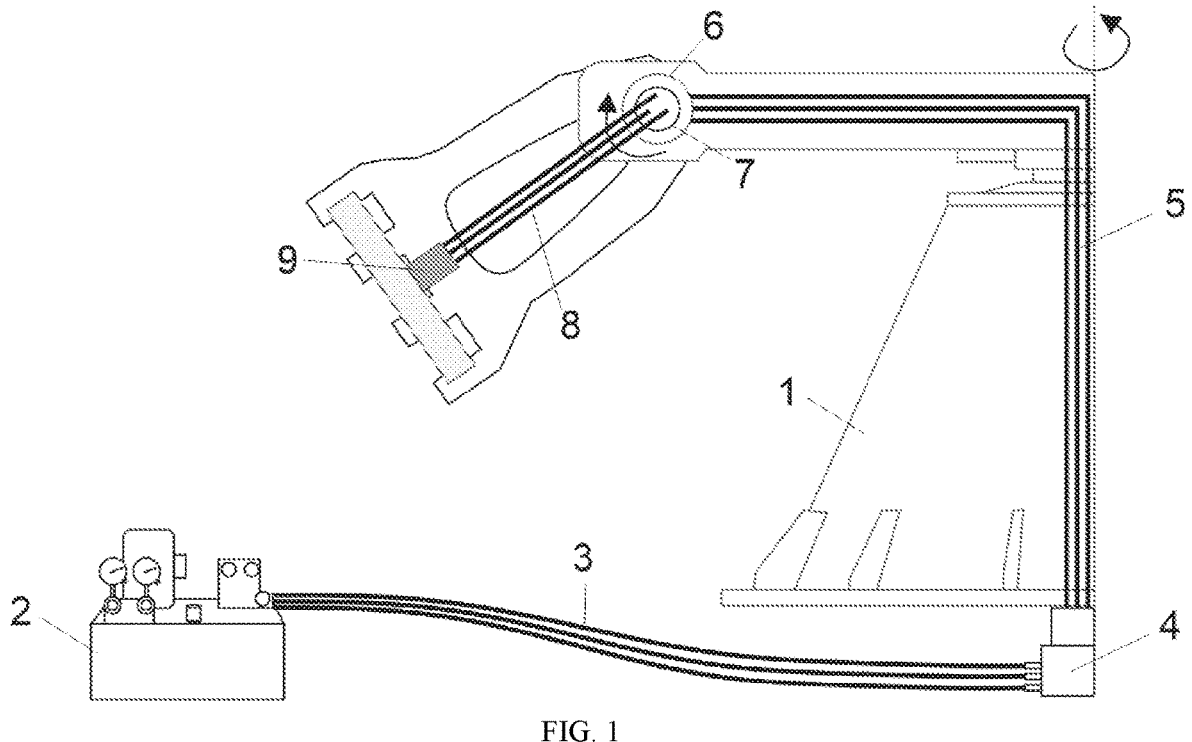
FIG. 1 is a schematic structural diagram of a liquid delivery system of an arm-centrifuge in a high centrifugal acceleration condition proposed by the present disclosure.

As shown in FIG. 1, the liquid delivery system of an arm-centrifuge in a high centrifugal acceleration condition provided by the present disclosure can meet the requirement of safe delivery of high-pressure oil in the centrifuge basket under the condition of a high centrifugal acceleration exceeding 200 g. The system includes a centrifuge main engine 1, a ground liquid source 2, a ground delivery conduit 3, a centrifuge bottom rotary joint 4, a centrifuge rotary arm delivery conduit 5, a rotary arm-basket pin roll 6, a basket rotary joint 7, a basket delivery conduit 8 and a basket conduit outlet 9.

The ground liquid source 2 includes a hydraulic source, a water source and the like, and is connected with the stator end of the centrifuge bottom rotary joint 4 through a high-pressure sealing threaded port through a ground delivery conduit 3.

The centrifuge bottom rotary joint 4 is fixed at the bottom of the centrifuge main engine 1, and its stator end is connected with the ground liquid source 2 through a conduit, and the centrifuge remains motionless during the rotation; the rotor end thereof is connected with the centrifuge rotary arm delivery conduit 5, and rotates with the rotation of the centrifuge during the rotation of the centrifuge, so as to realize delivery the liquid with specific flow and pressure provided by the stationary ground liquid source into the rotary centrifuge.

The centrifuge rotary arm delivery conduit 5 is inside the centrifuge, one end of which is connected with the rotor end 4 of the centrifuge bottom rotary joint and the other end of which is connected with the basket rotary joint 7; the centrifuge rotary arm delivery conduit 5 rotates with the rotation of the centrifuge during the rotation of the centrifuge.

Figure 2:
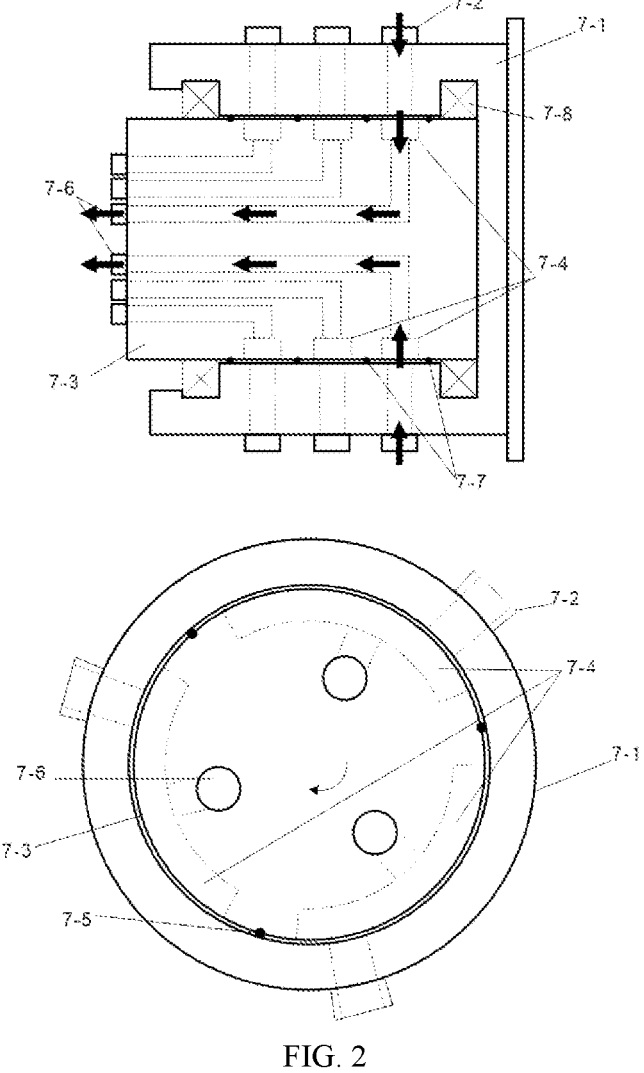
FIG. 2 is a schematic diagram of the rotary joint of the basket.

As shown in FIG. 2, the basket rotary joint 7 consists of a stator 7-1, a stator input interface 7-2, a rotor 7-3, a rotor output interface 7-6 and ball bearings 7-8. The rotor 7-3 is cylindrical, and the surface of the rotor 7-3 is engraved with a plurality of arc-shaped launders 7-4, and the radian of these arc-shaped launders 7-4 is θ, and three arc-shaped launders 7-4 can be uniformly arranged on a circumference; the three arc-shaped launders 7-4 are a group, and an axial annular sealing component 7-7 is arranged between different groups of launders to prevent fluids from interfering with each other; round rectangular sealing components 7-5 are arranged around the three launders of each group to prevent the fluids in the group from interfering with each other; the arrangement of the double seal components can ensure that the fluid in each launder remain independent and prevent the interference of pressure and medium between launders; the bottom of each arc-shaped launder 7-4 is perforated and communicated with the rotor output interface 7-6 through an axial passageway; the stator 7-1 is cylindrical, sleeved outside the rotor 7-3, and can rotate relative to the rotor 7-3 through the cooperation of ball bearings 7-8, and can ensure the stability of the gap and meet the sealing requirements under super gravity; and the stator 7-1 is provided with the stator input interface 7-2 in an opening at a position corresponding to each arc-shaped launder 7-4 on the rotor 7-3, and the stator input interface 7-2 is always communicated with the launder of a radian of θ on the rotor 7-3 during the 90-degree rotation of the rotor 7-3 relative to the stator 7-1, thereby communicating with the rotor output interface 7-6.

The method for determining the radian θ of the arc-shaped launder 7-4 is as follows:

assuming that the inner diameter of the stator input interface 7-2 is d, the outer diameter of the rotor is D, and the circumferential safety seal spacing between launders is f, then θ should satisfy:

$$90° + \frac{360° d}{\pi D} < \theta < 120° - \frac{360° f}{\pi D}$$

In this embodiment, the radian θ is 100 degrees, and the stator 7-1 of the basket rotary joint 7 is fixedly connected to the rotary arm-basket pin roll 6 through a flange, and the stator remains motionless during the rotation of the basket; and the stator input interface 7-2 is connected with the centrifuge rotary arm delivery conduit 5.

The basket delivery conduit 8 is a rigid pipe fixed on the basket, and its interface in the basket is a basket conduit outlet 9, which will provide high-pressure liquid delivery capacity for devices in the basket; the basket delivery conduit 8 is rigidly connected with the rotor output interface 7-6 of the basket rotary joint 7; during the 90-degree rotation of the basket, the basket delivery conduit 8 drives the rotor 7-3 of the basket rotary joint 7 to rotate 90 degrees together, while the stator 7-1 remains motionless, and the arc-shaped launder 7-4 of the rotor 7-3 is always communicated with the stator input interface 7-2 during the 90-degree rotation of the rotor 7-3 relative to the stator 7-1.

Those skilled in the art can easily make various changes and modifications according to the written description, drawings and claims provided by the present disclosure without departing from the spirit and scope of the present disclosure defined by the claims. Any modification or equivalent change to the above-mentioned embodiment according to the technical idea and essence of the present disclosure falls into the protection scope defined by the claims of the present disclosure.

What is claimed is:

1. A high-pressure liquid delivery system under a high centrifugal acceleration condition on an arm-centrifuge, comprising a centrifuge main engine, a ground liquid source, a ground delivery conduit, a centrifuge bottom rotary joint, a centrifuge rotary arm delivery conduit, a rotary arm-basket pin roll, a basket rotary joint, a basket delivery conduit and a basket conduit outlet;

wherein the centrifuge bottom rotary joint is fixed at a bottom of the centrifuge main engine, and a stator end of the centrifuge bottom rotary joint is connected with the ground liquid source by the ground delivery conduit, so that the centrifuge remains motionless during rotation; a rotor end of the centrifuge bottom rotary joint is connected with one end of the centrifuge rotary arm delivery conduit and rotates with the rotation of the centrifuge during the rotation of the centrifuge; and one other end of the centrifuge rotary arm delivery conduit is connected with the basket rotary joint;

wherein the basket rotary joint comprises a stator, a stator input interface, a rotor and a rotor output interface; wherein three arc-shaped launders as one group are uniformly arranged on one circumference of the rotor; a axial annular sealing component is arranged between each group of the launders, and a rounded rectangular sealing component is arranged around the three launders of each group; and a radian of the arc-shaped launder is θ, which can meet the following:

$$90° + \frac{360° d}{\pi D} < \theta < 120° - \frac{360° f}{\pi D}$$

where d is an inner diameter of an stator input interface, D is an outer diameter of the rotor, and f is a circumferential safety sealing distance between the launders; wherein the bottom of the each arc-shaped launder is communicated with the rotor output interface; the stator is sleeved outside the rotor; and the stator is provided with the stator input interface in an opening at a position corresponding to the each arc-shaped launder on the rotor;

wherein the stator of the basket rotary joint is fixedly connected to the rotary arm-basket pin roll, and the stator remains motionless during the rotation of the basket; and the stator input interface is connected with the centrifuge rotary arm delivery conduit; and wherein the basket delivery conduit is fixed on the basket, and an interface thereof in the basket is the basket conduit outlet; the basket delivery conduit is rigidly connected with the rotor output interface of the basket rotary joint; and the basket delivery conduit drives the rotor of the basket rotary joint to rotate together during the rotation of the basket, and the stator input interface is always communicated with the arc-shaped launder on the corresponding rotor during the rotation of the rotor relative to the stator, thereby communicating with the rotor output interface.

2. The high-pressure liquid delivery system under a high centrifugal acceleration condition on an arm-centrifuge according to claim 1, wherein the ground liquid source comprises a hydraulic oil source and a water source.

3. The high-pressure liquid delivery system under a high centrifugal acceleration condition on an arm-centrifuge according to claim 1, wherein the ground delivery conduit is connected with the stator end of the centrifuge bottom rotary joint through a sealing threaded port.

4. The high-pressure liquid delivery system under a high centrifugal acceleration condition on an arm-centrifuge according to claim 1, wherein the stator and the rotor are fitted by a ball bearing to rotate relatively by 90 degrees.

* * * * *